United States Patent

Akieda et al.

Patent Number: 5,144,083
Date of Patent: Sep. 1, 1992

[54] PROCESS FOR PRODUCING P-HYDROXYNEOPHYL M-PHENOXYBENZYL ETHER

[75] Inventors: Hideyuki Akieda; Naoki Sato; Koichi Morinaga; Yoshinori Ide; Ryuichi Mita; Mitsumasa Umemoto, all of Omuta, Japan

[73] Assignee: Mitsui Toatsu Chemicals, Incorporated, Tokyo, Japan

[21] Appl. No.: 591,637

[22] Filed: Oct. 2, 1990

[30] Foreign Application Priority Data

Oct. 3, 1989 [JP] Japan .................. 1-256985
Oct. 5, 1989 [JP] Japan .................. 1-258874
Oct. 5, 1989 [JP] Japan .................. 1-258875

[51] Int. Cl.$^5$ ................................ C07C 41/01
[52] U.S. Cl. .............................. 568/636; 568/637
[58] Field of Search .................. 568/637, 638, 636

[56] References Cited

U.S. PATENT DOCUMENTS 4,782,094 11/1988 Numata et al. .................. 514/721

OTHER PUBLICATIONS

Tiecco, *Journal of Synthetic Organic Chemistry*, pp. 749–758, Feb. 1988.
Weygand & Hilgetag, Preparative Organic Chemistry, p. 395, (1974).

Primary Examiner—Marianne Cintins
Assistant Examiner—Margaret Argo
Attorney, Agent, or Firm—Millen, White & Zelano

[57] ABSTRACT

A process for producing a p-hydroxyneophyl m-phenoxybenzyl ether represented by the general formula (II)

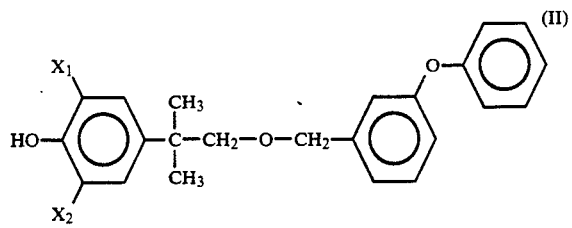

($X_1$ and $X_2$ are independently a hydrogen atom or a halogen atom) by subjecting a corresponding p-alkoxyneophyl m-phenoxybenzyl ether represented by the general formula (I)

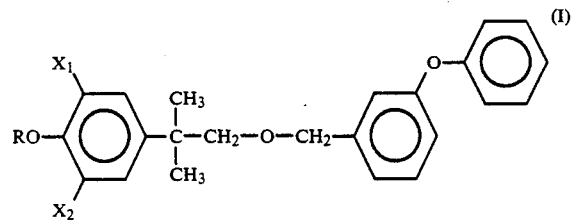

(R represents a lower alkyl group, and $X_1$ and $X_2$ have the same definitions as above) to ether cleavage, in which process the ether cleavage reaction is effected in an aprotic polar solvent, using a lower alkoxide of an alkali metal or an alkaline earth metal or using a metal hydroxide in the presence of a lower alcohol.

27 Claims, No Drawings

PROCESS FOR PRODUCING P-HYDROXYNEOPHYL M-PHENOXYBENZYL ETHER

The present invention relates to a process for producing a p-hydroxyneophyl m-phenoxybenzyl ether which is useful as an intermediate in agricultural chemicals production.

It is known in Japanese Patent Application Kokai (Laid-Open) No. 45233/1988 that difluorohalomethoxyphenyl type compounds represented by the following formula (III)

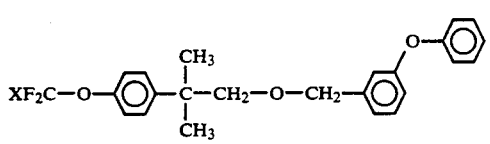

(X represents a bromine atom or a chlorine atom) have superior insecticidal and Acaricidal activities and are useful as an agricultural chemical.

In producing a compound of the formula (III), a p-hydroxyneophyl m-phenoxybenzyl ether represented by the following formula (II)

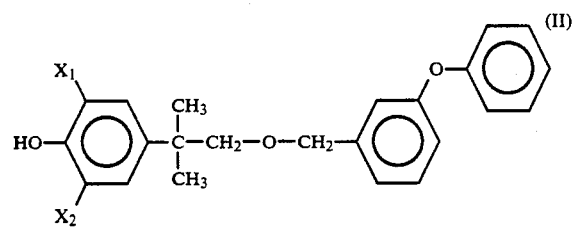

($X_1$ and $X_2$ are independently a hydrogen atom or a halogen atom) is an important intermediate.

That is, a compound of the formula (III) can be produced by reacting a compound of the formula (II) ($X_1=X_2=H$) with dibromodifluoromethane or bromochlorodifluoromethane.

With respect to the production of the compound of the formula (II), there is known only a process disclosed in Japanese Patent Application Kokai (Laid-Open) No. 212335/1987. The document discloses a process for producing 3-chloro-4-hydroxyneophyl m-phenoxybenzyl ether [a compound of the formula (II) wherein $X_1=Cl$ and $X_2=H$] by subjecting 4-ethoxy-3-chloroneophyl m-phenoxybenzyl ether to an ether cleavage reaction. It is specifically a process comprising subjecting 4-ethoxy-3-chloroneophyl m-phenoxybenzyl ether to ether cleavage in N,N'-dimethylimidazolidinone, using excessive potassium hydroxide as an ether cleavage agent. According to the document, 4-hydroxy-3-chloroneophyl m-phenoxybenzyl ether was obtained under the reaction conditions of 150° C. and 18 hours, but the yield was as low as about 50%.

The confirmation test and investigation by the present inventors indicated that in the above process using potassium hydroxide as an ether cleavage agent, the elevation in reaction temperature could increase the conversion, but brought about the formation of by-products such as tar-like substance and the like and reduced the selectivity of p-alkoxyneophyl m-phenoxybenzyl ether to p-hydroxyneophyl m-phenoxybenzyl ether and that the optimization of reaction conditions in order to reduce said problems gave a yield of p-hydroxyneophyl m-phenoxybenzyl ether of only about 70% at the highest. Also in the above process, the above results were obtained when there was used, as the p-alkoxyneophyl m-phenoxybenzyl ether, an ether compound having a halogen atom at the o-position of the alkoxy group; however, when there was used an ether compound having a hydrogen atom at the o-position of the alkoxy group, the proceeding of ether cleavage reaction was very difficult presumably due to the very low reactivity of the alkoxy group and the yield did not reach even 10%.

Meanwhile, there are generally known various processes for cleavage of ether compound, such as a process using a strong acid (e.g. hydrobromic acid, hydroiodic acid), a process using pyridine hydrochloride or a boron halide, and a process using a Lewis acid. When these processes are applied to a p-alkoxyneophyl m-phenoxybenzyl ether, however, the conversion of said ether to a corresponding p-hydroxyneophyl m-phenoxybenzyl ether at a satisfying yield is impossible.

It is an object of the present invention to provide a process which can provide a hydroxyneophyl m-phenoxybenzyl ether under relatively mild conditions, smoothly, almost selectively and at a high yield and accordingly which has a high industrial value.

According to the present invention, there is provided, as a process capable of achieving the above object, a process for producing a p-hydroxyneophyl m-phenoxybenzyl ether represented by the general formula (II)

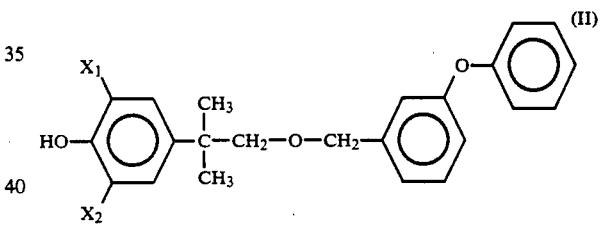

($X_1$ and $X_2$ are independently a hydrogen atom or a halogen atom) by subjecting a corresponding p-alkoxyneophyl m-phenoxybenzyl ether represented by the general formula (I)

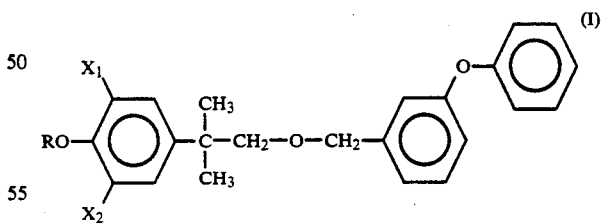

(R represents a lower alkyl group, and $X_1$ and $X_2$ have the same definitions as above) to ether cleavage, in which process the ether cleavage reaction is effected in an aprotic polar solvent, using a lower alkoxide of an alkali metal or an alkaline earth metal or using a metal hydroxide in the presence of a lower alcohol.

In the formula (I), the lower alkyl group represented by R refers to alkyl groups of 1-4 carbon atoms, and specifically includes a methyl group, an ethyl group, a n-propyl group, an isopropyl group, a n-butyl group, an isobutyl group, a sec-butyl group and a tert-butyl group. Also in the formula (I), the halogen atom represented by $X_1$ or $X_2$ is a fluorine, chlorine, bromine or iodine atom.

Specific examples of the compound of the formula (I) used in the present invention include p-methoxyneophyl m-phenoxybenzyl ether, p-ethoxyneophyl m-phenoxybenzyl ether, p-n-propoxyneophyl m-phenoxybenzyl ether, p-isopropoxyneophyl m-phenoxybenzyl ether, p-n-butoxyneophyl m-phenoxybenzyl ether, p-sec-butoxyneophyl m-phenoxybenzyl ether, p-isobutoxyneophyl m-phenoxybenzyl ether, 3-chloro (or bromo)-4-methoxyneophyl m-phenoxybenzyl ether, 3-chloro (or bromo)-4-ethoxyneophyl m-phenoxybenzyl ether, 3-chloro (or bromo)-4-n-propoxyneophyl m-phenoxybenzyl ether, 3-chloro (or bromo)-4-isopropoxyneophyl m-phenoxybenzyl ether, 3-chloro (or bromo)-4-n-butoxyneophyl m-phenoxybenzyl ether, 3-chloro (or bromo)-4-sec-butoxyneophyl m-phenoxybenzyl ether, 3-chloro (or bromo)-4-isobutoxyneophyl m-phenoxybenzyl ether, 3,5-dichloro (or dibromo)-4-methoxyneophyl m-phenoxybenzyl ether, 3,5-dichloro (or dibromo)-4-ethoxyneophyl m-phenoxybenzyl ether, 3,5-dichloro (or di-bromo)-4-n-propoxyneophyl m-phenoxybenzyl ether, 3,5-dichloro (or dibromo)-4-isopropoxyneophyl m-phenoxybenzyl ether, 3,5-dichloro (or dibromo)-4-n-butoxyneophyl m-phenoxybenzyl ether, 3,5-dichloro (or dibromo)-4-sec-butoxyneophyl m-phenoxybenzyl ether, 3,5-dichloro (or dibromo)-4-isobutoxyneophyl m-phenoxybenzyl ether, 3-bromo-5-chloro-4-methoxyneophyl m-phenoxybenzyl ether, 3-bromo-5-chloro-4-ethoxyneophyl m-phenoxybenzyl ether, 3-bromo-5-chloro-4-n-propoxyneophyl m-phenoxybenzyl ether, 3-bromo-5-chloro-4-isopropoxyneophyl m-phenoxybenzyl ether, 3-bromo-5-chloro-4-n-butoxyneophyl m-phenoxybenzyl ether, 3-bromo-5-chloro-4-sec-butoxyneophyl m-phenoxybenzyl ether and 3-bromo-5-chloro-4-isobutoxyneophyl m-phenoxybenzyl ether.

As the aprotic polar solvent used in the present invention, there is preferred a nitrogen-containing aprotic polar solvent or a sulfur-containing aprotic polar solvent. Specific examples of the nitrogen-containing aprotic polar solvent include N,N-dimethylformamide, N,N'-dimethylformamide, N,N-dimethylacetamide, N,N-dimethylacetamide, N-methylpyrrolidone, N-ethylpyrrolidone, N,N'-dimethylimidazolidinone and N,N'-dimethylpropyleneurea. Specific examples of the sulfur-containing aprotic polar solvent include dimethyl sulfoxide or sulfolane, methylmethylsulfinylmethyl sulfide and methylthiomethyl-p-tolylsulfone. Of these, preferable is dimethylsulfoxide or sulfolane, and more preferable is dimethyl sulfoxide.

These solvents are ordinarily used alone but may be used in combination of two or more.

The amount of the solvent used is ordinarily 0.5 part by weight or more, preferably 1 part by weight or more per 1 part by weight of the compound (I).

The solvent preferably contains no or substantially no water, but may contain water in such an amount that the object of the present invention is not impaired.

Description is made below on the process using a metal alkoxide as an ether cleavage agent.

The lower alkoxide of an alkali metal or an alkaline earth metal specifically includes lithium lower alkoxides, sodium lower alkoxides, potassium lower alkoxides, calcium lower alkoxides, magnesium lower alkoxides, etc. Of these, sodium lower akloxides and potassium lower alkoxides are preferred. Potassium tert-butoxide, in particular, gives the most favorable result.

The amount of the metal alkoxide used is preferably at least 1 equivalent relative to the compound (I) as a material. The reason is that when the amount is less than the theoretical amount (1 equivalent), the intended ether cleavage reaction proceeds but the material compound (I) remains unreacted in a large amount, making the separation of the product from the material complicated in the posttreatment step after the reaction. The amount of the metal alkoxide used has no particular upper limit but is used ordinarily in an amount of 5 equivalents or less relative to the compound (I), from the economical standpoint.

In the present invention, the order of feeding the material, the solvent and the metal alkoxide as an ether cleavage agent has no particular restriction. For example, the raw material compound of the formula (I) is dissolved in the solvent; to the resulting solution is fed the metal alkoxide; the resulting mixture is heated and subjected to a reaction at 50°-200° C., preferably 80°-150° C. In this case, the reaction atmosphere can be any of an ordinary atmosphere and an inert atmosphere such as nitrogen or the like.

The reaction time cannot be determined by a specific rule depending upon the amount of the metal alkoxide used, the reaction temperature, etc., but the reaction is complete ordinarily in one hour or less.

Next, description is made on the process using a metal hydroxide as an ether cleavage agent.

This process is effected using a metal hydroxide as an ether cleavage agent for the compound of the formula (I) in the presence of a lower alcohol. The metal of the metal hydroxide specifically includes alkali metals or alkaline earth metals and more specifically includes lithium, sodium, potassium, rubidium, cesium, beryllium, magnesium, calcium, strontium, barium, etc. Potassium is preferable.

When the amount of the metal hydroxide used is too small, the ether cleavage reaction is slow and does not proceed sufficiently. When the amount is too excessive, side reactions tend to occur. Therefore, the metal hydroxide is used in a range of 1-10 moles, preferably 1.5-8 moles per 1 mole of the compound (I).

The lower alcohol used is preferably an alcohol of 1-4 carbon atoms. Specifically, there is preferred methanol, ethanol, n-propanol, isopropanol, n-butanol, sec-butanol, isobutanol or tert-butanol. In this invention, one of these alcohols are used in combination with the metal hydroxide to allow the ether cleavage reaction to proceed smoothly and selectively. These alcohols may be used in combination of two or more. The amount of the alcohol used is ordinarily 0.1-20 moles, preferably 0.5-10 moles per 1 mole of the ether of the formula (I).

In the present invention, the order of feeding the material, the solvent, the metal hydroxide and the lower alcohol is not particularly restricted. For example, the material compound of the formula (I) is dissolved in the solvent; into the resulting solution are fed the metal hydroxide and the lower alcohol; the resulting mixture is heated and subjected to a reaction ordinarily at 50°-200° C., preferably at 80°-150° C. The reaction atmosphere can be any of an ordinary atmosphere and an inert atmosphere such as nitrogen or the like.

The reaction time cannot be determined by a specific rule depending upon the amounts of the metal hydroxide and lower alcohol used, the reaction temperature, etc., but the reaction is complete ordinarily in 20 hours or less.

The process of effecting the ether cleavage reaction using the metal hydroxide, as compared with the process of effecting said reaction using the lower alkoxide, is advantageous in the facility for material preparation as well as in the safety.

When there is used a material compound (I) having no halogen atom at the o-position of the alkoxy group, the increase in yield is generally difficult. However, even in such a case, when the ether cleavage reaction is effected according to the present process using a lower alcohol and a metal hydroxide in a sulfur-containing aprotic polar solvent, an intended product can be obtained at a high yield.

In any of the above two processes, the completion of the reaction can be easily known by using a means such as thin-layer chromatography, high-performance liquid chromatography or the like.

After the ether cleavage reaction, the product of the formula (II), i.e. p-hydroxyneophyl m-phenoxybenzyl ether can be isolated from the reaction system according to various methods. For example, the reaction mixture is poured into water and then made acidic with hydrochloric acid or sulfuric acid; the resulting mixture is extracted with an organic solvent such as benzene or the like; the extract is subjected to distillation to remove the solvent; the residue is subjected to sludging with a solvent such as n-hexane or the like; or the residue is subjected to vacuum distillation, column chromatography or the like; thereby, the product can be isolated easily.

Specific examples of the compound of the formula (II) produced by the present process are 4-hydroxyneophyl m-phenoxybenzyl ether, 3-chloro-4-hydroxyneophyl m-phenoxybenzyl ether, 3-bromo-4-hydroxyneophyl m-phenoxybenzyl ether, 3,5-dichloro-4-hydroxyneophyl m-phenoxybenzyl ether, 3,5-dibromo-4-hydroxyneophyl m-phenoxybenzyl ether and 3-bromo-5-chloro-4-hydroxyneophyl m-phenoxybenzyl ether.

The present invention is described in detail below by way of Examples.

In the Examples, the following analytical conditions were employed for high performance liquid chromatography.

Analytical Conditions for High Performance Liquid Chromatography

Column: YMC Pack A-312 (ODS); 6 mm (diameter)×15 cm
Eluting solution: $CH_3CN/H_2O = 10/1$ (volume ratio)
Flow rate: 0.4 ml/min
Detector: Ultraviolet spectrophotometer (wavelength: 254 nm)

EXAMPLE 1

Synthesis of 3-chloro-4-hydroxyneophyl m-phenoxybenzyl ether

Into a 1-l four-necked flask were fed 123.3 g (0.3 mol) of 3-chloro-4-ethoxyneophyl m-phenoxybenzyl ether, 50.5 g (0.45 mol) of potassium tert-butoxide and 450 g of N,N'-dimethylimidazolidinone. The mixture was subjected to a reaction at 120° C. for 5 hours.

After the completion of the reaction, the reaction mixture was poured into 1,000 ml of ice water. The resulting mixture was adjusted to pH 5-6 with a 10% aqueous hydrochloric acid solution. The organic layer was extracted three times each with 500 ml of benzene. The benzene layer washed with waters and dried with anhydrous sodium sulfate.

Sodium sulfate was removed by filtration, and the filtrate was subjected to distillation under vacuum to remove benzene to obtain 118.7 g of a brown oily matter. This oily matter was analyzed by high performance liquid chromatography and showed a content of 3-chloro-4-hydroxyneophyl m-phenoxybenzyl ether of 93.1% (a yield of 96.2% relative to 3-chloro-4-ethoxyneophyl m-phenoxybenzyl ether).

The oily matter was further subjected to sludging with 1,000 ml of n-hexane to obtain white 3-chloro-hydroxyneophyl m-phenoxybenzyl ether in an amount of 105.8 g (a yield of 92% relative to 3-chloro-4-ethoxyneophyl m-phenoxybenzyl ether).

The product gave the following IR spectrum and NMR spectrum data.

IR ($cm^{-1}$) (KBr tablet method): 1590, 1500, 1455, 1260, 1225, 1200, 1170, 1150, 1115, 1070, 1020, 780, 700

NMR δ H (solvent: $CDCl_3$): 1.32 (6H, s), 3.42(2H, s), 4.45(2H, s), 6.8–7.5 (12H, m)

Melting point (°C.): 68–69

Elemental analysis (%): Found: C 72.40, H 6.01, Cl 9.13. Cal.: C 72.15, H 6.05, Cl 9.26.

EXAMPLE 2

Synthesis of 4-hydroxyneophyl m-phenoxybenzyl ether

Into a 1-l four-necked flask were fed 116.6 g (0.3 mol) of 4-ethoxyneophyl m-phenoxybenzyl ether, 50.5 g (0.45 mol) of potassium tert-butoxide and 450 g of N,N'-dimethylpropyleneurea. The resulting mixture was subjected to a reaction at 140° C. for 5 hours.

After the completion of the reaction, the reaction mixture was poured into 1,000 ml of ice water. The resulting mixture was adjusted to pH 5–6 with a 10% aqueous hydrochloric acid solution. The organic layer was extracted three times each with 500 ml of benzene. The benzene layer was washed with water and dried with anhydrous sodium sulfate.

Sodium sulfate was removed by filtration, and the filtrate was subjected to distillation under vacuum to remove benzene to obtain 103.0 g of a brown oily matter. This oily matter was analyzed by high performance liquid chromatography and showed a content of 4-hydroxyneophyl m-phenoxybenzyl ether of 94.6% (a yield of 93.2% relative to 4-ethoxyneophyl m-phenoxybenzyl ether)

The oily matter was further subjected to sludging with 100 ml of n-hexane for purification to obtain white 4-hydroxyneophyl m-phenoxybenzyl ether in an amount of 95.5 g (a yield of 91.3% relative to 4-ethoxyneophyl m-phenoxybenzyl ether).

IR ($cm^{-1}$) (KBr tablet method): 3400, 1610, 1515, 1485, 1440, 1240, 1210, 825, 755, 690, 675

NMR δ H (solvent: $CDCl_3$): 2.43 (2H, t), 5.52(1H, broad, s), 6.56–7.38(13H, m)

Melting point (°C.): 69.0–70.0

Elemental analysis (%): Found: C 79.41, H 6.87. Cal.: C 79.28, H 6.94.

EXAMPLE 3–6

Ether cleavage reactions were effected by using various aromatic ether compounds as a material, various solvents and various metal alkoxides. The results are shown in Table 1.

After each other cleavage reaction, the reaction mixture was poured into water. The resulting mixture was acidified with hydrochloric acid and then extracted with benzene. The benzene layer was washed with water and subjected to distillation to remove benzene, to obtain a crude product of a corresponding aromatic hydroxy compound.

Each crude product was analyzed by high performance liquid chromatography.

The results are shown in Table 1.

The oily matter was further subjected to hexane sludging for separation and purification; however, the crystals of the intended product could not be isolated because there presented large amounts of by-products.

COMPARATIVE EXAMPLE 2

Into a 1-l four-necked flask were fed 116.6 g (0.3 mol) of 4-ethoxyneophyl m-phenoxybenzyl ether, 70.7 g (1.2 mol) of flaky potassium hydroxide and 450 g of 2-methyl-2-propanol. The resulting mixture was refluxed for

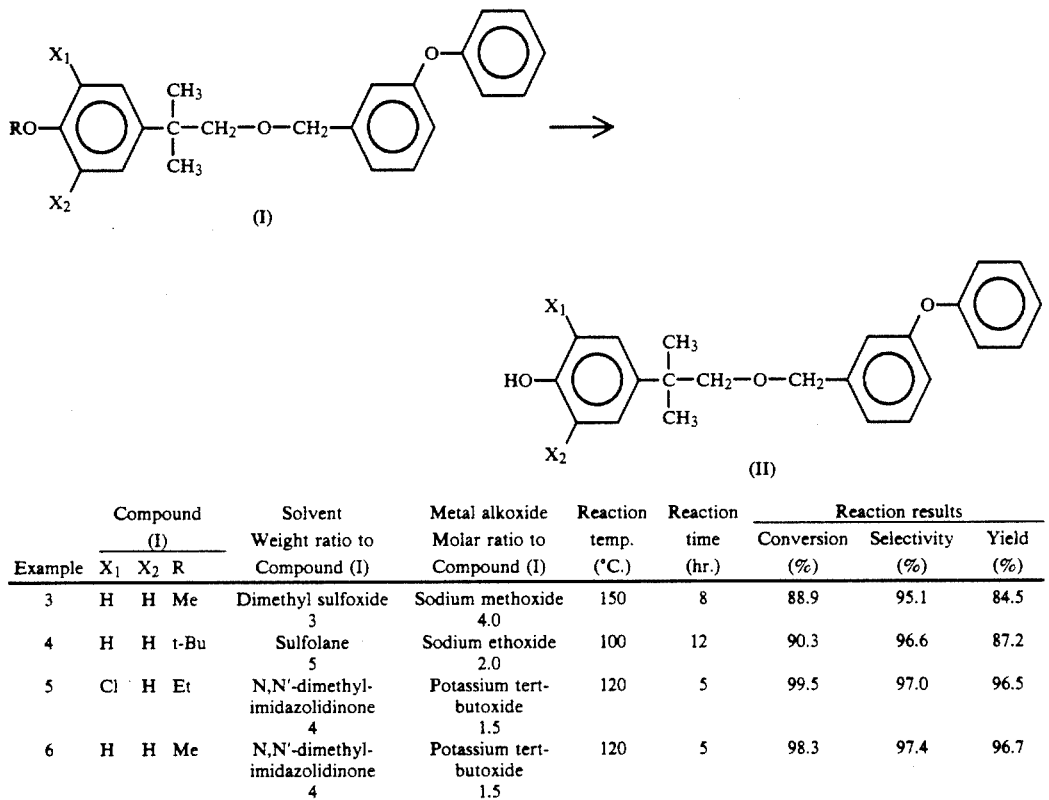

|  | Compound (I) | | | Solvent | Metal alkoxide | Reaction | Reaction | Reaction results | | |
|---|---|---|---|---|---|---|---|---|---|---|
|  |  | | | Weight ratio to | Molar ratio to | temp. | time | Conversion | Selectivity | Yield |
| Example | $X_1$ | $X_2$ | R | Compound (I) | Compound (I) | (°C.) | (hr.) | (%) | (%) | (%) |
| 3 | H | H | Me | Dimethyl sulfoxide 3 | Sodium methoxide 4.0 | 150 | 8 | 88.9 | 95.1 | 84.5 |
| 4 | H | H | t-Bu | Sulfolane 5 | Sodium ethoxide 2.0 | 100 | 12 | 90.3 | 96.6 | 87.2 |
| 5 | Cl | H | Et | N,N'-dimethyl-imidazolidinone 4 | Potassium tert-butoxide 1.5 | 120 | 5 | 99.5 | 97.0 | 96.5 |
| 6 | H | H | Me | N,N'-dimethyl-imidazolidinone 4 | Potassium tert-butoxide 1.5 | 120 | 5 | 98.3 | 97.4 | 96.7 |

Test method: A compound (I) (0.3 mol), a solvent and a metal alkoxide were fed into a 1-liter four necked flask. The resulting mixture was subjected to a reaction under given conditions.

COMPARATIVE EXAMPLE 1

Into a 1-l four-necked flask were fed 123.3 g (0.3 mol) of 3-chloro-4-ethoxyneophyl m-phenoxybenzyl ether, 70.7 g (1.2 mol) of 95% flaky potassium hydroxide and 450 g of N,N'-dimethylimidazolidinone. The resulting mixture was subjected to a reaction at 120° C. for 5 hours.

After the completion of the reaction, the reaction mixture was poured into 1,000 ml of ice water. The resulting mixture was adjusted to pH 5-6 with a 10% aqueous hydrochloric acid solution. The organic layer was extracted three time each with 500 ml of benzene. The benzene layer was washed with water and dried with anhydrous sodium sulfate.

Sodium sulfate was removed by filtration, and the filtrate was subjected to distillation under vacuum to remove benzene to obtain 122.2 g of a brown oily matter. This oily matter was analyzed by high performance liquid chromatography and showed a content of 3-chloro-4-hydroxyneophyl m-phenoxybenzyl ether of 35.1% (a yield of 34.8% relative to 3-chloro-4-hydroxyneophyl m-phenoxybenzyl ether).

24 hours with heating. The post-treatment was effected in the same manner as in Comparative Example 1 to obtain 116.1 g of an oily matter. Analysis by high performance liquid chromatography showed no formation of intended 4-hydroxyneophyl m-phenoxybenzyl ether and ended in recovery of raw material.

EXAMPLE 7

Synthesis of 3-chloro-4-hydroxyneophyl m-phenoxybenzyl ether

Into a 1-l four-necked flask were fed 123.3 g (0.3 mol) of 3-chloro-4-ethoxyneophyl m-phenoxybenzyl ether, 70.7 g (1.2 mol) of 95% flaky potassium hydroxide, 10 g (0.135 mol) of tert-butanol and 450 g of N,N'-dimethylimidazolidinone. The mixture was subjected to a reaction at 120° C. for 5 hours.

After the completion of the reaction, the reaction mixture was poured into 1,000 ml of ice water. The resulting mixture was adjusted to pH 5-6 with a 10% aqueous hydrochloric acid solution. The organic layer was extracted three times each with 500 ml of benzene.

The benzene layer was washed with water and dried with anhydrous sodium sulfate.

Sodium sulfate was removed by filtration, and the filtrate was subjected to distillation under vacuum to remove benzene to obtain 119.0 g of a brown oily matter. This oily matter was analyzed by high performance liquid chromatography and showed a content of 3-chloro-4-hydroxyneophyl m-phenoxybenzyl ether of 95.1% (a yield of 98.5% relative to 3-chloro-4-ethoxyneophyl m-phenoxybenzyl ether).

The oily matter was further subjected to sludging with 1,000 ml of hexane to obtain white 3-chloro-4-hydroxyneophyl m-phenoxybenzyl ether in an amount of 109.8 g (a yield of 95.6% relative to 3-chloro-4-ethoxyneophyl m-phenoxybenzyl ether).

Elemental analysis (%): Found: C 72.40, H 6.01, Cl 9.13. Cal. : C 72.15, H 6.05, Cl 9.26.

IR (cm$^{-1}$) (KBr tablet method): 1590, 1500, 1455, 1260, 1225, 1200, 1170, 1150, 1115, 1070, 1020, 780, 700

NMR $\delta$ H (solvent: CDCl$_3$): 1.32 (6H, s), 3.42(2H, s), 4.45(2H, s), 6.8–7.5(12H, m)

Melting point (°C.): 68–69

EXAMPLE 8

Synthesis of 4-hydroxyneophyl m-phenoxybenzyl ether

Into a 1-l four-necked flask were fed 116.6 g (0.3 mol) of 4-ethoxyneophyl m-phenoxybenzyl ether. 70.7 g (1.2 mol)) of 95% flaky potassium hydroxide, 10 g (0.135 mol) of n-butanol and 450 g of N,N'-dimethylpropyleneurea. The mixture was subjected to a reaction at 120° C. for 5 hours.

After the completion of the reaction, the reaction mixture was poured into 1,000 ml of ice water. The resulting mixture was adjusted to pH 5–6 with a 10% aqueous hydrochloric acid solution. The organic layer was extracted three times each with 500 ml of benzene. The benzene layer was washed with water and dried with anhydrous sodium sulfate.

Sodium sulfate was removed by filtration, and the filtrate was subjected to distillation under vacuum to remove benzene to obtain 108.4 g of a brown oily matter. This oily matter was analyzed by high performance liquid chromatography and showed a content of 4-hydroxyneophyl m-phenoxybenzyl ether of 58.7% (a yield of 60.9% relative to 4-ethoxyneophyl m-phenoxybenzyl ether).

The oily matter was further subjected to sludging with 1,000 ml of hexane for purification to obtain white 4-hydroxyneophyl m-phenoxybenzyl ether in an amount of 60.4 g (a yield of 57.8% relative to 4-ethoxyneophyl m-phenoxybenzyl ether).

Elemental analysis (%): Found: C 79.41, H 6.87. Cal. : C 79.28, H 6.94.

IR (cm$^{-1}$) (KBr tablet method): 3400, 1610, 1515, 1485, 1440, 1240, 1210, 825, 755, 690, 675

NMR $\delta$ H (solvent: CDCl$_3$): 2.43 (2H, t), 5.52(1H, broad, s), 6.56–7.38(13H, m)

Melting point (°C.): 69.0–70.0

EXAMPLE 9

Into a 1-l four-necked flask were fed 108.7 g (0.3 mol) of 4-methoxyneophyl m-phenoxybenzyl ether, 70.7 g (1.2 mol) of 95% flaky potassium hydroxide, 10 g (0.217 mol) of ethanol and 450 g of N,N'-dimethylimidazolidinone. The mixture was subjected to a reaction at 120° C. for 5 hours.

After the completion of the reaction, the reaction mixture was poured into 1,000 ml of ice water. The resulting mixture was adjusted to pH 5–6 with a 10% aqueous hydrochloric acid solution. The organic layer was extracted three times each with 500 ml of benzene. The benzene layer was washed with water and dried with anhydrous sodium sulfate.

Sodium sulfate was removed by filtration, and the filtrate was subjected to distillation under vacuum to remove benzene to obtain 109.4 g of a brown oily matter. This oily matter was analyzed by high performance liquid chromatography and showed a content of p-hydroxyneophyl m-phenoxybenzyl ether of 79.5% (a yield of 83.2% relative to 4-methoxyneophyl m-phenoxybenzyl ether).

The oily matter was further subjected to sludging with 1,000 ml of hexane for purification to obtain white p-hydroxyneophylm-phenoxybenzyl ether in an amount of 78.5 g (a yield of 75.1% relative to 4-methoxyneophyl m-phenoxybenzyl ether).

EXAMPLE 10

Into a 1-l four-necked flask were fed 123.3 g (0.3 mol) of 3-chloro-4-ethoxyneophyl m-phenoxybenzyl ether, 70.7 g (1.2 mol) of 95% flaky potassium hydroxide, 10 g (0.312 mol) of methanol and 450 g of N,N'-dimethylpropyleneurea. The mixture was subjected to a reaction at 110° C. for 7 hours.

After the completion of the reaction, the reaction mixture was poured into 1,000 ml of ice water.

The resulting mixture was adjusted to pH 5–6 with a 10% aqueous hydrochloric acid solution. The organic layer was extracted three times each with 500 ml of benzene. The benzene layer was washed with water and dried with anhydrous sodium sulfate.

Sodium sulfate was removed by filtration, and the filtrate was subjected to distillation under vacuum to remove benzene to obtain 118.6 g of a brown oily matter. This oily matter was analyzed by high performance liquid chromatography and showed a content of p-hydroxyneophyl m-phenoxybenzyl ether of 90.1% (a yield of 93.0% relative to 3-chloro-4-ethoxyneophyl m-phenoxybenzyl ether).

The oily matter was further subjected to sludging with 1,000 ml of hexane for purification to obtain white 3-chloro-4-hydroxyneophyl m-phenoxybenzyl ether in an amount of 103.8 g (a yield of 90.4% relative to 3-chloro-4-ethoxyneophyl m-phenoxybenzyl ether).

COMPARATIVE EXAMPLE 3

Into a 1-l four-necked flask were fed 123.3 g (0.3 mol) of 3-chloro-4-ethoxyneophyl m-phenoxybenzyl ether, 70.7 g (1.2 mol) of 95% flaky potassium hydroxide, and 450 g of N,N'-dimethylimidazolidinone. The mixture was subjected to a reaction at 120° C. for 5 hours.

After the completion of the reaction, the reaction mixture was poured into 1,000 ml of ice water. The resulting mixture was adjusted to pH 5–6 with a 10% aqueous hydrochloric acid solution. The organic layer was extracted three times each with 500 ml of benzene. The benzene layer was washed with water and dried with anhydrous sodium sulfate Sodium sulfate was removed by filtration, and the filtrate was subjected to distillation under vacuum to remove benzene to obtain 122.2 g of a brown oily matter. This oily matter was analyzed by high performance liquid chromatography and showed a content of 3-chloro-4-hydroxyneophyl m-phenoxybenzyl ether of 35.1% (a yield of 34.8% relative to 3-chloro-4-ethoxyneophyl m-phenoxybenzyl ether).

The oily matter was further subjected to hexane sludging for purification; however, the crystals of the intended product could not be isolated because there were present large amounts of by-products.

COMPARATIVE EXAMPLE 4

Into a 1-l four-necked flask were fed 116.6 g (0.3 mol) of 4-ethoxyneophyl m-phenoxybenzyl ether, 70.7 g (1.2 mol) of 95% flaky potassium hydroxide, and 450 g of N,N'-dimethylpropyleneurea. The mixture was subjected to a reaction at 120° C. for 5 hours.

After the completion of the reaction, the reaction mixture was poured into 1,000 ml of ice water. The resulting mixture was adjusted to pH 5-6 with a 10% aqueous hydrochloric acid solution. The organic layer was extracted three times each with 500 ml of benzene. The benzene layer was washed with water and dried with anhydrous sodium sulfate.

Sodium sulfate was removed by filtration, and the filtrate was subjected to distillation under vacuum to remove benzene to obtain 172.2 g of a brown oily matter. This oily matter was analyzed by high performance liquid chromatography and showed a content of 4-hydroxyneophyl m-phenoxybenzyl ether of 6.9% (a yield of 8.4% relative to 4-ethoxyneophyl m-phenoxybenzyl ether).

The oily matter was further subjected to sludging with 1,000 ml of hexane; however, the unreacted material and by-products were present in large amounts and no corresponding 4-hydroxyneophyl m-phenoxybenzyl ether was formed.

EXAMPLE 11

Synthesis of 4-hydroxyneophyl m-phenoxybenzyl ether

Into a 1-l four-necked flask were fed 116.6 g (0.3 mol) of 4-ethoxyneophyl m-phenoxybenzyl ether, 70.7 g (1.2 mol) of 95% flaky potassium hydroxide, and 10 g of tert-butanol and 450 g of dimethyl sulfoxide. The mixture was subjected to a reaction at 120° C. for 5 hours.

After the completion of the reaction, the reaction mixture was poured into 1,000 ml of ice water. The resulting mixture was adjusted to pH 5-6 with a 10% aqueous hydrochloric acid solution. The organic layer was extracted three times each with 500 ml of benzene. The benzene layer was washed with water and dried with anhydrous sodium sulfate.

Sodium sulfate was removed by filtration, and the filtrate was subjected to distillation under vacuum to remove benzene to obtain 110.3 g of a brown oily matter. This oily matter was analyzed by high performance liquid chromatography and showed a content of 4-hydroxyneophyl m-phenoxybenzyl ether 95.2% (a yield of 97.2% relative to 4-ethoxyneophyl m-phenoxybenzyl ether).

The oily matter was further subjected to sludging with 500 ml of hexane for purification to obtain 101.8 g of white 4-hydroxyneophyl m-phenoxybenzyl ether (94.2% relative to 4-ethoxyneophyl m-phenoxybenzyl ether).

Elemental analysis (%): Found: C 79.41, H 6.87. Cal. : C 79.28, H 6.94.

IR (cm$^{-1}$) (KBr tablet method): 3400, 1610, 1515, 1485, 1440, 1240, 1210, 825, 755, 690, 675

NMR δ H (solvent: CDCl$_3$): 2.43 (2H, t), 5.52(1H, broad, s), 6.56–7.38(13H, m)

Melting point (°C.): 69.2–70.0

EXAMPLE 12

Synthesis of 3-chloro-4-hydroxyneophyl m-phenoxybenzyl ether

Into a 1-l four-necked flask were fed 123.3 g (0.3 mol) of 3-chloro-4-ethoxyneophyl m-phenoxybenzylether, 70.7 g (1.2 mol) of 95% flaky potassium hydroxide, and 10 g of tert-butanol and 450 g of dimethyl sulfoxide. The mixture was subjected to a reaction at 110° C. for 7 hours.

After the completion of the reaction, the reaction mixture was poured into 1,000 ml of ice water. The resulting mixture was adjusted to pH 5-6 with a 10% aqueous hydrochloric acid solution. The organic layer was extracted three times each with 500 ml of benzene. The benzene layer was washed with water and dried with anhydrous sodium sulfate.

Sodium sulfate was removed by filtration, and the filtrate was subjected to distillation under vacuum to remove benzene to obtain 117.3 g of a brown oily matter. This oily matter was analyzed by high performance liquid chromatography and showed a content of 3-chloro-4-hydroxyneophyl n-phenoxybenzyl ether 95.2% (a yield of 97.9% relative to 3-chloro-4-ethoxyneophyl m-phenoxybenzyl ether).

The oily matter was further subjected to sludging with 500 ml of hexane for purification to obtain 109.1 g of white 3-chloro-4-hydroxyneophyl m-phenoxybenzyl ether (95.0% relative to 3-chloro-4-ethoxyneophyl m-phenoxybenzyl ether).

Elemental analysis (%): Found: C 72.40, H 6.01, Cl 9.13. Cal.: C 72.15, H 6.05, Cl 9.26.

IR (cm$^{-1}$) (KBr tablet method): 1590, 1600, 1455, 1260, 1225, 1200, 1170, 1150, 1115, 1070, 1020, 780, 700

NMR δ H (solvent: CDCl$_3$): 1.32 (6H, s), 3.42(2H, s), 4.45(2H, s), 6.8–7.5 (12H, m)

Melting point (°C.): 68.0–69.0

EXAMPLE 13

The same reaction as in Example 11 was effected except that 4-ethoxyneophyl m-phenoxybenzyl ether was replaced by 108.7 g (0.3 mol) of 4-methoxyneophyl m-phenoxybenzyl ether. After the completion of the reaction, the same post-treatment as in Example 11 was applied to obtain 107.1 g of a brown oily matter. As a result of high performance liquid chromatography, the content of 4-hydroxyneophyl m-phenoxybenzyl ether was 94.2% (a yield of 96.5% relative to 4-methoxyneophyl m-phenoxybenzyl ether).

COMPARATIVE EXAMPLE 5

Into a 1-l four-necked flask were fed 116.6 g (0.3 mol) of 4-ethoxyneophyl m-phenoxybenzyl ether, 70.7 g (1.2 mol) of 95% flaky potassium hydroxide, and 10 g of tert-butanol and 450 g of dimethyl sulfoxide. The mixture was subjected to a reaction at 120° C. for 5 hours.

After the completion of the reaction, the reaction mixture was poured into 1,000 ml of ice water. The resulting mixture was adjusted to pH 5-6 with a 10% aqueous hydrochloric acid solution. The organic layer was extracted three times each with 500 ml of benzene. The benzene layer was washed with water and dried with anhydrous sodium sulfate.

Sodium sulfate was removed by filtration, and the filtrate was subjected to distillation under vacuum to remove benzene to obtain 110.1 g of a brown oily matter. This oily matter was analyzed by high performance liquid chromatography and showed a content of 4-hydroxyneophyl m-phenoxybenzyl ether 48.3% (a yield of 50.9% relative to 4-ethoxyneophyl m-phenoxybenzyl ether).

The oily matter was further subjected to sludging with 500 ml of hexane; however, it was impossible to obtain crystals of p-hydroxyneophyl m-phenoxybenzyl ether of high purity.

In the process of the present invention, the ether cleavage reaction of alkoxyneophyl m-phenoxybenzyl ether of the formula (I) proceeds smoothly and almost selectively under relatively mild conditions, and there can be obtained, at a high yield, a hydroxyneophyl m-phenoxybenzyl ether of the formula (II) which is useful as an intermediate for production of certain agricultural chemicals. Accordingly, the process of the present invention has a high industrial value.

I claim:

1. A process for producing a p-hydroxyneophyl m-phenoxybenzyl ether represented by the formula (II)

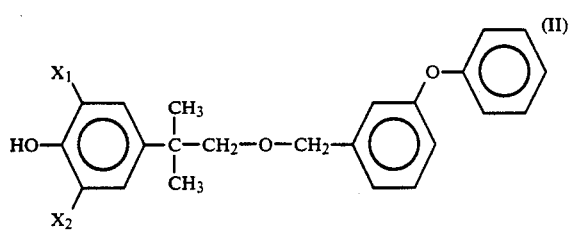

wherein $X_1$ and $X_2$ are independently a hydrogen atom or a halogen atom by subjecting a corresponding p-alkoxyneophyl m-phenoxybenzyl ether represented by the formula (I)

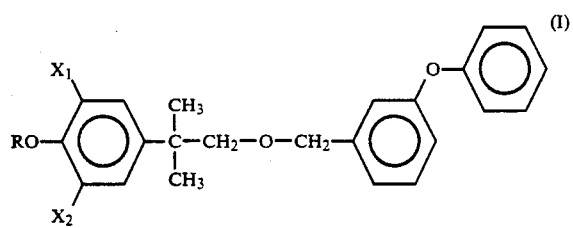

wherein R represents a lower alkyl group, and $X_1$ and $X_2$ have the same definitions as above to ether cleavage, in which process the ether cleavage reaction is effected in an aprotic polar solvent, using a lower alkoxide of an alkali metal or of an alkaline earth metal or using a metal hydroxide in the presence of a lower alcohol.

2. A process according to claim 1, wherein the aprotic polar solvent is at least one solvent selected from the group consisting of N,N'-dimethylformamide, N,N-dimethylformamide, N,N-dimethylacetamide, N,N-dimethylacetamide, N-methylpyrrolidone, N-ethylpyrrolidone, N,N-dimethylimidazolidinone, N,N'-dimethylpropyleneurea, dimethyl sulfoxide and sulfolane.

3. A process according to claim 1, wherein the lower alkoxide of an alkali metal or an alkaline earth metal is a lower alkoxide of sodium or potassium.

4. A process according to claim 1, wherein the lower alkoxide of an alkali metal or an alkaline earth metal is potassium tert-butoxide.

5. A process according to claim 1, wherein the lower alkoxide of an alkali metal or an alkaline earth metal is used in an amount of 1-5 equivalents relative to the p-alkoxyneophyl m-phenoxybenzyl ether of the formula (I).

6. A process according to claim 1, wherein the lower alcohol is a lower alcohol of 1-4 carbon atoms.

7. A process according to claim 1, wherein the lower alcohol is used in an amount of 0.1-20 moles per 1 mole of the p-alkoxyneophyl m-phenoxybenzyl ether of the formula (I).

8. A process according to claim 1, wherein the metal hydroxide is a hydroxide of an alkali metal or an alkaline earth metal.

9. A process according to claim 1, wherein the metal hydroxide is potassium hydroxide.

10. A process according to claim 1, wherein the metal hydroxide is used in an amount of 1-10 equivalents relative to the p-alkoxyneophyl m-phenoxybenzyl ether of the formula (I).

11. A process according to claim 1, wherein the cleavage is effected at a reaction temperature of 50°-200° C.

12. A process for producing a p-hydroxyneophyl m-phenoxybenzyl ether of the formula (II)

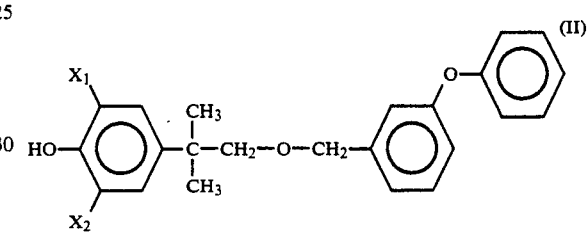

wherein $X_1$ and $X_2$ are independently a hydrogen atom or a halogen atom, which comprises selectively cleaving the p-ether group of a corresponding p-alkoxyneophyl m-phenoxybenzyl ether represented by the formula (I)

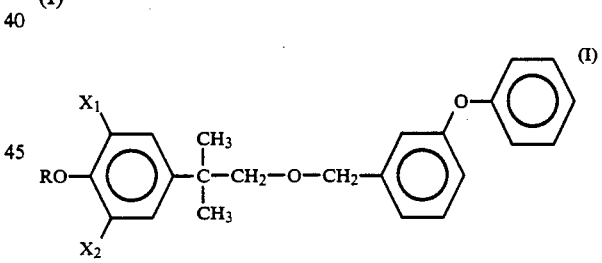

wherein R represents a lower alkyl group, and $X_1$ and $X_2$ have the same definitions as above) to ether cleavage, in which process the ether cleavage is effected in an aprotic polar solvent, in the presence of a lower alkoxide of an alkali metal or an alkaline earth metal.

13. A process according to claim 12, wherein the lower alkoxide of an alkali metal or an alkaline earth metal is a lower alkoxide of sodium or potassium.

14. A process according to claim 12, wherein the lower alkoxide of an alkali metal or an alkaline earth metal is potassium tert-butoxide.

15. A process according to claim 12, wherein the lower alkoxide of an alkali metal or an alkaline earth metal is used in an amount of 1 equivalent or more relative to the p-alkoxyneophyl m-phenoxybenzyl ether of the formula (I).

16. A process according to claim 12, wherein the aprotic polar solvent is at least one solvent selected from the group consisting of N,N'-dimethylformamide, N,N-dimethylformamide, N,N-dimethylacetamide, N,N-dimethylacetamide, N-methylpyrrolidone, N-ethylpyrrolidone, N,N'-dimethylimidazolidinone, N,N'-dimethylpropyleneurea, dimethyl sulfoxide and sulfolane.

17. A process according to claim 12, wherein the aprotic polar solvent is N,N'-dimethylimidazolidinone, N,N'-dimethylpropyleneurea, dimethyl sulfoxide or sulfolane.

18. A process for producing a p-hydroxyneophyl m-phenoxybenzyl ether of the formula II

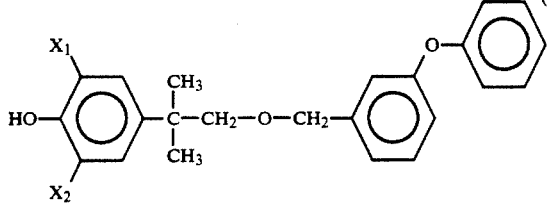

wherein $X_1$ and $X_2$ are independently a hydrogen atom or a halogen atom, which comprises selectively cleaving the p-ether group of a corresponding p-alkoxyneophyl m-phenoxybenzyl ether represented by the formula (I)

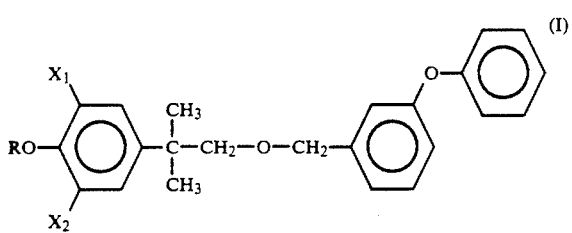

wherein R represents a lower alkyl group, and $X_1$ and $X_2$ have the same definitions as above, in a nitrogen-containing aprotic polar solvent, using a metal hydroxide in the presence of a lower alcohol.

19. A process according to claim 18, wherein the aprotic polar solvent is at least one solvent selected from the group consisting of N,N'-dimethylformamide, N,N-dimethylformamide, N,N-dimethylacetamide, N,N-dimethylacetamide, N-methylpyrrolidone, N-ethylpyrrolidone, N,N'-dimethylimidazolidinone and N,N'-dimethylpropylene-urea.

20. A process according to claim 18, wherein the aprotic polar solvent is N,N'-dimethylimidazolidinone or N,N'-dimethylpropyleneurea.

21. A process according to claim 18, wherein the lower alcohol is a lower alcohol of 1–4 carbon atoms.

22. A process according to claim 18, wherein the lower alcohol is used in an amount of 0.1–20 moles per 1 mole of the compound of the formula (I).

23. A process for producing a p-hydroxyneophyl m-phenoxybenzyl ether represented by the formula (II)

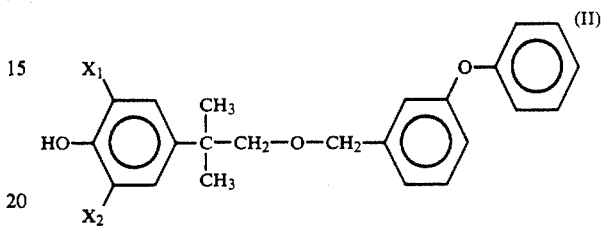

wherein $X_1$ and $X_2$ are independently a hydrogen atom or a halogen atom, which comprises selectively cleaving the p-ether group of a corresponding p-alkoxyneophyl m-phenoxybenzyl ether represented by the formula (I)

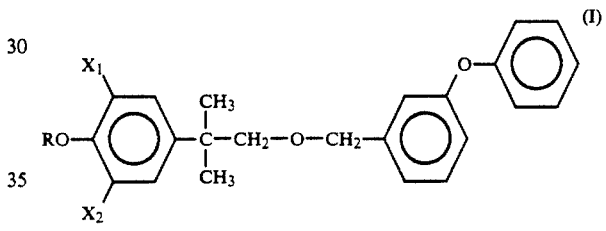

wherein R represents a lower alkyl group, and $X_1$ and $X_2$ have the same definitions as above, in a sulfur containing aprotic polar solvent, using a metal hydroxide in the presence of a lower alcohol.

24. A process according to claim 23, wherein the aprotic polar solvent is dimethyl sulfoxide or sulfolane.

25. A process according to claim 23, wherein the aprotic polar solvent is dimethyl sulfoxide.

26. A process according to claim 23, wherein the lower alcohol is a lower alcohol of 1–4 carbon atoms.

27. A process according to claim 23, wherein the lower alcohol is used in an amount of 0.1–20 moles per 1 mole of the compound of the formula (I).

* * * * *